United States Patent
Koellner et al.

(10) Patent No.: US 6,414,486 B1
(45) Date of Patent: Jul. 2, 2002

(54) MAGNETIC RESONANCE IMAGING APPARATUS AND METHOD FOR OBTAINING MULTIPLE EXPOSURES AT RESPECTIVELY DIFFERENT POSITIONS WITHOUT INTERRUPTION

(75) Inventors: Richard Koellner, Weisendorf; Frank Rabe, Erlangen, both of (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 09/317,829

(22) Filed: May 25, 1999

(30) Foreign Application Priority Data

May 29, 1998 (DE) .......................................... 198 24 203

(51) Int. Cl.$^7$ ................................................. G01V 3/00
(52) U.S. Cl. ........................ 324/309; 324/307; 324/318
(58) Field of Search ................................ 324/309, 307, 324/318

(56) References Cited

U.S. PATENT DOCUMENTS

| | | |
|---|---|---|
| 5,138,260 A | 8/1992 | Molyneaux et al. |
| 5,208,537 A | 5/1993 | Rietsch et al. |
| 5,423,315 A * | 6/1995 | Margosian et al. .......... 324/309 |
| 5,657,757 A * | 8/1997 | Hurd et al. ................. 324/307 |
| 5,924,987 A * | 7/1999 | Meaney et al. ............. 324/306 |

FOREIGN PATENT DOCUMENTS

| | | |
|---|---|---|
| EP | 0 114 405 | 12/1982 |
| EP | 0 654 675 | 5/1995 |

* cited by examiner

*Primary Examiner*—Edward Lefkowitz
*Assistant Examiner*—Dixomara Vargas
(74) *Attorney, Agent, or Firm*—Schiff Hardin & Waite

(57) ABSTRACT

A magnetic resonance imaging apparatus has a magnet with at least one patient receptacle and at least one support plate, as well as a predetermined number of transmit and/or receive coils. In at least two predetermined exposure positions, at least one exposure respectively takes place using predetermined adjustment parameters. High-contrast exposures can be obtained in a short time, by the required adjustment parameters being determined in a preceding adjustment process, and the exposures are carried out in a subsequent exposure process.

12 Claims, 2 Drawing Sheets

FIG. 2
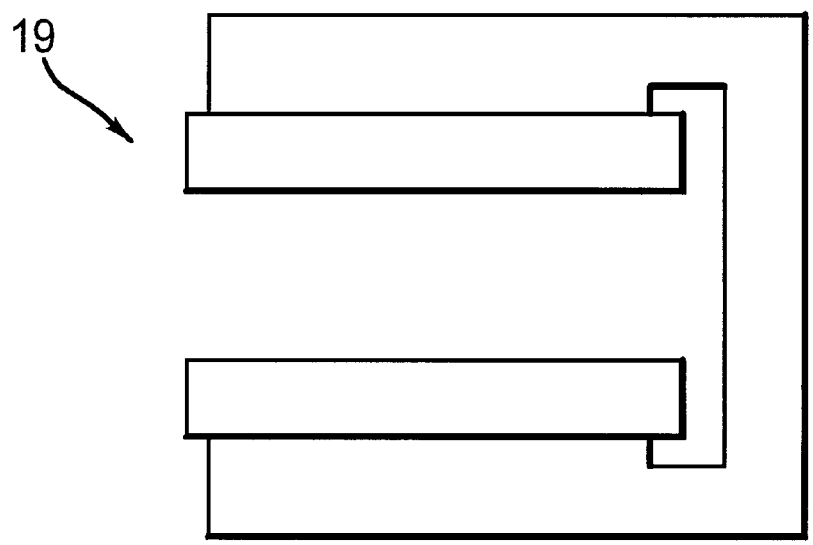
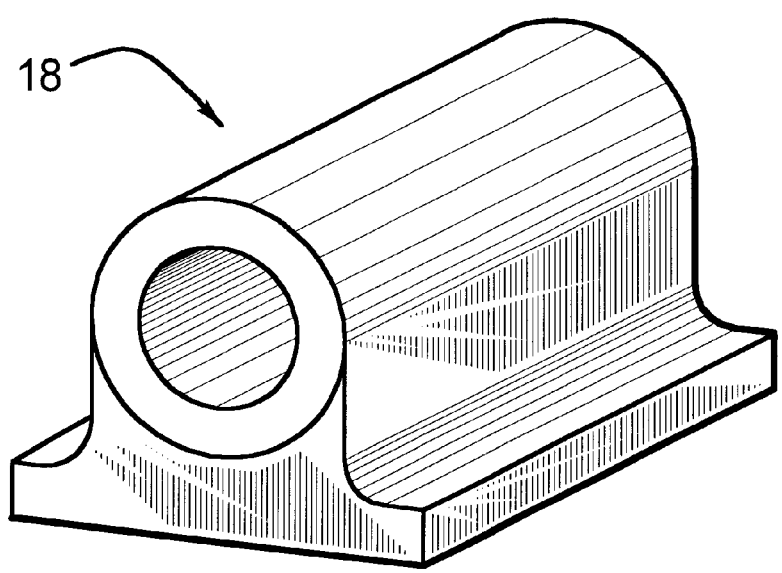
FIG. 3

MAGNETIC RESONANCE IMAGING APPARATUS AND METHOD FOR OBTAINING MULTIPLE EXPOSURES AT RESPECTIVELY DIFFERENT POSITIONS WITHOUT INTERRUPTION

BACKGROUND OF THE INVENTION

1. Field of the Invention

The present invention relates to a magnetic resonance imaging apparatus of the type having a magnet with at least one patient receptacle and at least one support plate, as well as a predetermined number of transmit and/or receive coils, and which allows exposures with the subject in at least two predetermined exposure positions, with at least one exposure taking place using predetermined adjustment parameters.

2. Description of the Prior Art

In known magnetic resonance imaging apparatuses, for different exposure positions the associated exposure parameters must in general be modified at least partially. The exposure parameters that may have to be modified include e.g. the position of the support plate and the connection or disconnection of transmit and/or receive coils. As a rule, a modification of the exposure parameters requires a readjustment of the magnetic resonance imaging apparatus.

The adjustment essentially serves to optimize the RF chain (transmit and receive coils and associated amplifiers) and to optimize the homogeneity of the main magnetic field produced by the magnet (also called the basic magnetic field or $B_0$ field) in a volume under examination (imaging volume) located inside the patient receptacle. Due to the necessary homogeneity of the examination volume, this volume is also called the homogeneity volume.

The exposure parameters are also patient-dependent, since the patient represents an attenuation or damping for the transmit and/or receive coils. A precise adjustment thus also serves for patient safety with respect to the RF exposure.

In general, known magnetic resonance imaging apparatuses recognize automatically whether the. exposure parameters belonging. to particular exposure positions must be modified, and carry out a readjustment if warranted.

This adjustment normally requires 10 to 90 seconds per exposure position. Given certain examination procedures, this time is not available. This includes e.g. the tracking of doses of contrast agent over a larger body region that exceeds the available homogeneity volume of the nuclear spin resonance apparatus. In such cases, the patient must be guided by displacement of the support plate in a manner corresponding to the flow of contrast agent. If a smaller viewing field is not acceptable, the readjustment that is thereby required per imaging measurement (exposure) requires a multiple dosage of contrast agent, which is not desirable for the patient.

Alternatively to a smaller viewing field or to multiple injections of contrast agent, it is possible after the first adjustment to omit the further adjustments (readjustments) inherently required for high-contrast exposures. However, this leads to a considerable worsening of the image quality.

SUMMARY OF THE INVENTION

An object of the present invention is to provide magnetic resonance imaging apparatus of the type described above that provides high-contrast exposures in a short time, even given an examination of larger body segments.

This object is achieved in accordance with the principles of the present invention in a magnetic resonance imaging apparatus having a magnet and at least one patient receptacle and at least one support plate, as well as a predetermined number of transmit and/or receive coils. At least in two predetermined exposure positions, an exposure respectively takes place using predetermined adjustment parameters. The required adjustment parameters are inventively determined in a preceding adjustment process, and the exposures are executed in a subsequent exposure process.

For example, the exposure parameters can be modified by means of a spatial modification of position (longitudinal displacement, transverse displacement, rotation) of the support plate within the patient receptacle. Alternatively, or in addition, a modification of the adjustment parameters can take place by connection and/or disconnection of the transmit coils and/or the receive coils.

In the inventive magnetic resonance imaging apparatus, the required adjustment parameters are not determined immediately before each individual exposure, as is conventional. Rather, the required adjustment parameters are determined in an adjustment process that precedes the exposure process. Only after the determination of the required adjustment parameters are the exposures carried out, in a separate imaging exposure process.

The adjustment parameters are of course stored at least until the conclusion of the examination. The adjustment parameters thus can be used again, when identical or suitably similar exposure parameters (position of the support plate and configuration of the transmit and/or receive coils) are again reached in the context of the same examination.

In examinations with the inventive apparatus, high-contrast exposures are thus obtained, since it is not necessary to omit an adjustment. Due to the fact that the adjustment is carried out in a separate adjustment process, and the adjustment parameters are stored until the conclusion of the examination, the transmit and receive coils, or their coil elements, can be switched quickly during the examination, so that, in addition, reduced examination times result.

The inventive solution is suitable for a large number of different forms of magnetic resonance imaging apparatuses. Thus, for example, the magnet can be fashioned as a cylindrical magnet (solenoid) or as a horseshoe magnet (C-arm apparatus). Given cylindrically shaped magnets, the patient receptacle is fashioned as a patient tube.

DESCRIPTION OF THE DRAWING

FIG. 2 schematically illustrates an embodiment of an apparatus in accordance with the invention, wherein the magnet which generates the basic magnetic field is a horseshoe magnet.

FIG. 3 schematically illustrates an embodiment of an apparatus in accordance with the invention, wherein the magnet which generates the basic magnetic field is a cylindrical magnet.

DESCRIPTION OF THE PREFERRED EMBODIMENTS

Figure 1:
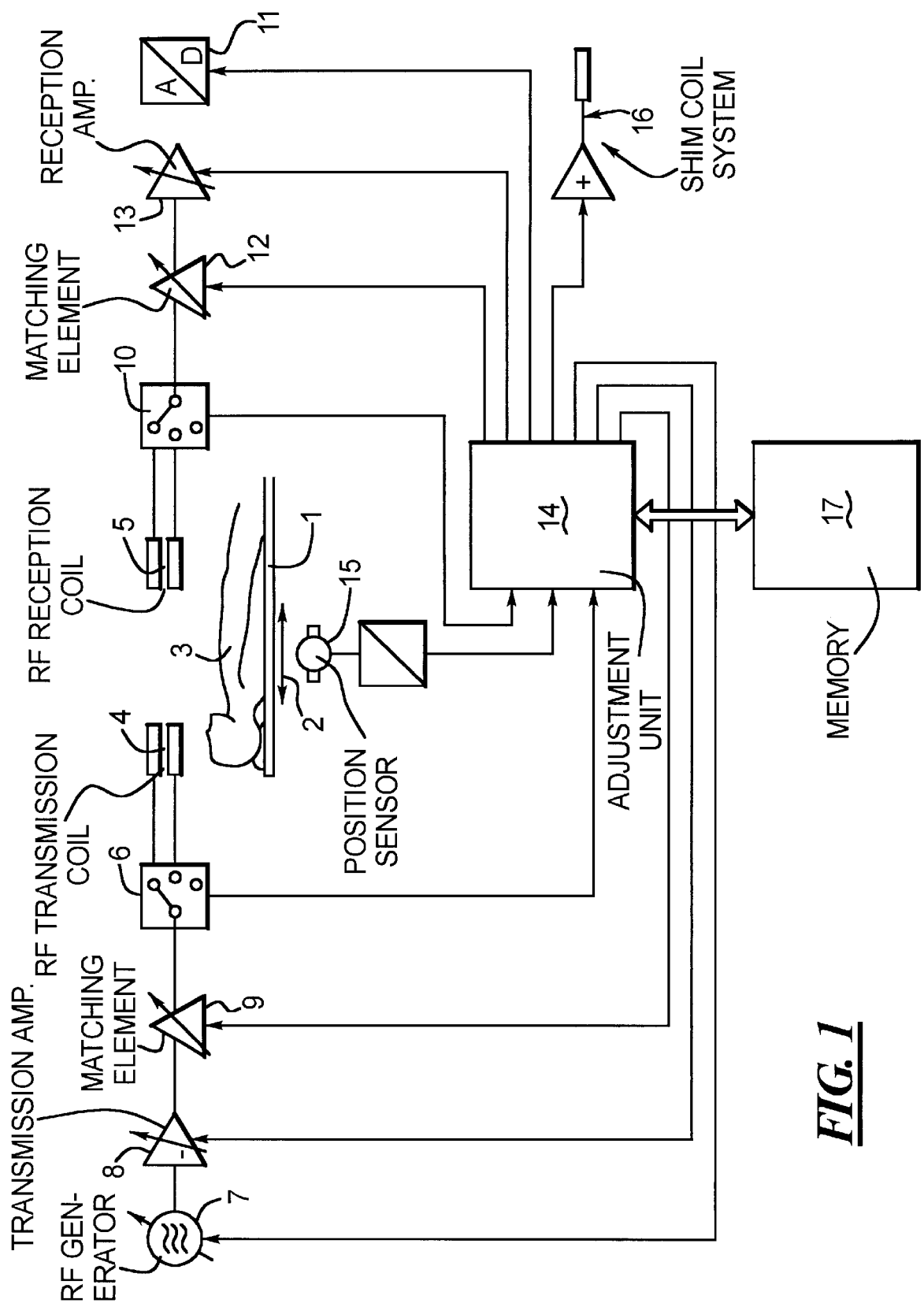
FIG. 1 is a schematic block diagram of a magnetic resonance imaging apparatus constructed and operating in accordance with principles of the present invention.

The apparatus in FIG. 1 has a support plate 1 that is arranged in longitudinally placeable fashion inside an examination volume of a magnet. Within the scope of invention, the magnet can for example a cylindrical magnet 18 as shown in FIG. 3 (solenoid) or a horseshoe magnet (C-arm) 19 as shown in FIG. 2. Given cylindrically shaped magnets, the patient receptacle is fashioned as a patient tube as own in FIG. 3.

The longitudinal displaceability of the support plate 1 is indicated with a double arrow 2. Due to the longitudinal displaceability of the support plate 1, larger body sections of a patient 3 lying on the support plate 1 can be examined.

The nuclear spin resonance apparatus shown in the drawing additionally has a predetermined number of transmit coils 4 and a predetermined number of receive coils 5.

The transmit coils 4 can be connected, in a desired configuration, to a generator 7 by means of a transmit coil changeover switch 6. The generator 7 supplies the transmit coils 4 with current via a-transmit amplifier 8 and via a matching element 9.

The receive coils 5 can be connected, in a desired configuration, to a receiver 11 by means of a receive coil changeover switch 10. The signals of the connected receive coils 5 are given to the receiver 11 via. a matching element 12 and via a receive amplifier 13.

The configurations of the transmit coils 4 and the receive coils 5, defined by the transmit coils changeover switch 6 and by the receive coils changeover switch 10, are supplied to an adjustment unit 14 as inputs.

As a further input, the position of the support plate 1, which is determined by a position sensor 15, is supplied to the adjustment unit 14.

The adjustment unit 14 processes the inputs that it has received from the transmit coils changeover switch 6, from the receive coils changeover switch 10, and from the position sensor 15, and at its output supplies corresponding control signals to the generator 7, to the transmit amplifier 8, to the matching elements 9 and 12, as well as to the receive amplifier 13 and to the receiver 11.

In addition, the adjustment unit 14 supplies a control signal to a shim coil system 16.

The inputs and the control signals (outputs) are stored, as adjustment parameters, in a memory 17 until the conclusion of the examination.

With the embodiment shown in the drawing of the inventive apparatus, larger bodily segments of the patient 3 can be examined. Such examinations are, for example, the tracking of doses of contrast agent over a larger body region, as carried out for example in subtraction angiography or in physiologically controlled imaging.

In the context of the preparation for measurement, which in the case of a peripheral angiography at the leg, includes slice positioning along the vascular tree, several measurements are already made without contrast agent. Due to the homogeneity volume of the magnet being too small, in these measurements the support plate 1 must be displaced, and so must be newly adjusted. The associated adjustment parameters for each position of the support plate 1 are stored in the memory 17. As additional adjustment parameters, the connected configuration of the transmit coils 4, as well as the connected configuration of the receive coils 5, are stored in the memory 17. In addition, the adjustment parameters include the corresponding control signals for the generator 7, for the transmit amplifier 8, for the matching elements 9 and 12, as well as for the receive amplifier 13, for the receiver 11 and for the shim coil system 16.

After the conclusion of the measurement preparation, which includes the determination of the adjustment parameters, the support plate 1 is guided back into the initial position, and the contrast agent is administered. In the imaging measurement that now takes place, each of the positions of the support plate 1 used in the measurement preparation is newly set in succession, and the transmit coils 4 and the receive coils 5 are connected as in the measurement preparation. Subsequently, an imaging measurement (exposure). is immediately carried out with the known adjustment parameters stored in the memory 17, i.e. without a new adjustment.

In the inventive apparatus, the required adjustment parameters are thus not determined immediately before each individual imaging measurement; rather, the required adjustment parameters are completely determined in a preceding adjustment process, in the context of the measurement preparation. According to the invention, the adjustment process thus precedes the exposure process. Only after the determination of the required adjustment parameters are the exposures (imaging measurement) carried out, in a separate exposure process. In examinations with the inventive apparatus, high-contrast exposures. are thereby obtained, since it is not necessary to omit an adjustment. In addition, due to the fact that the adjustment parameters are stored in a memory 17 until the conclusion of the examination, reduced examination times result. Due to the short examination times, in subtraction angiography the course of the contrast agent can thus be tracked without chronological gaps.

Although modifications and changes may be suggested by those skilled in the art, it is the intention of the inventors to embody within the patent warranted hereon all changes and modifications as reasonably and properly come within the scope of their contribution to the art.

We claim as our invention:

1. A magnetic resonance imaging apparatus comprising:
   a magnet having a patient receptacle;
   a patient support plate which is movable relative to said patient receptacle;
   a plurality of RF coils for exciting and receiving magnetic resonance signals in an examination subject during an exposure of said examination subject;
   said support plate being movable relative to said receptacle to at least two predetermined exposure positions in an exposure procedure, with at least one exposure using said RF coils taking place at each of said exposure positions, said exposures respectively requiring different predetermined adjustment parameters and also being movable to said at least two predetermined exposure positions in an adjustment procedure entirely preceding said exposure procedure to obtain said adjustment parameters; and
   a memory for storing said adjustment parameters obtained in said adjustment procedure entirely preceding said exposure procedure, and for allowing readout of said adjustment parameters during said exposure procedure to allow said exposure procedure to proceed without interruption.

2. An apparatus as claimed in claim 1 wherein said adjustment parameters are modified respectively for said exposures by a spatial change of position of said support plate within said receptacle.

3. An apparatus as claimed in claim 1 wherein said adjustment parameters are modified by a selected connection and disconnection of said RF coils.

4. An apparatus as claimed in claim 1 wherein said magnet comprises a cylindrical magnet, and wherein said patient receptacle comprises a patient tube inside said cylindrical magnet.

5. An apparatus as claimed in claim 1 wherein said magnet comprises a horseshoe magnet.

6. A magnetic resonance imaging apparatus as claimed in claim 1 comprising an adjustment unit connected to RF coils for adjusting operation of said RF coils in said at least two predetermined exposure positions in said adjustment procedure to obtain said adjustment parameters.

7. A magnetic resonance imaging apparatus as claimed in claim 1 further comprising shim coils, and an adjustment unit connected to said shim coils and to said RF coils and wherein said adjustment unit adjusts operation of said shim coils at said at least two predetermined exposure positions in said adjustment procedure to obtain said adjustment parameters.

8. A magnetic resonance imaging apparatus as claimed in claim 7 wherein said adjustment unit is also connected to said RF coils and wherein said adjustment unit adjusts operation of said RF coils, together with said operation of said shim coils, at said at least two predetermined exposure positions in said adjustment procedure to obtain said adjustment parameters.

9. A method for operating a magnetic resonance imaging apparatus having a magnet with a patient receptacle, comprising the steps of:

placing a patient on a support plate which is movable relative to said patient receptacle;

in an adjustment procedure, moving said support plate and said patient to at least two predetermined exposure positions in said receptacle and obtaining adjustment parameters at each of said exposure positions;

storing said adjustment parameters; and conducting an exposure procedure, following said adjustment procedure, with said examination subject on said support plate being moved to each of said exposure positions and reading out said adjustment parameters from said memory during said exposure procedure for each of said exposure positions so that said exposure procedure is conducted without interruption.

10. A method as claimed in claim 9 wherein the step of conducting an exposure procedure comprises conducting an exposure procedure using RF coils and wherein the step of obtaining said adjustment parameters in each of said exposure positions in said adjustment procedure comprises obtaining adjustment parameters for said RF coils at each of said exposure positions in said adjustment procedure.

11. A method as claimed in claim 9 wherein the step of conducting an exposure procedure comprises conducting an exposure procedure using shim coils and wherein the step of obtaining said adjustment parameters in each of said exposure positions in said adjustment procedure comprises obtaining adjustment parameters for said shim coils at each of said exposure positions in said adjustment procedure.

12. A method as claimed in claim 11 wherein the step of conducting an exposure procedure comprises conducting an exposure procedure with RF coils in addition to said shim coils, and wherein the step of obtaining said adjustment parameters at each of said exposure positions comprises obtaining adjustment parameters for said RF coils, in addition to said adjustment parameters for said shim coils, at each of said exposure positions in said adjustment procedure.

\* \* \* \* \*